United States Patent [19]

Matsumoto et al.

[11] 4,418,687
[45] Dec. 6, 1983

[54] ELECTRIC SLEEP INDUCER

[75] Inventors: Junji Matsumoto, Tokushima; Shohei Kamiya; Yasuhiko Sugihara, both of Tokyo, all of Japan

[73] Assignee: Homer Ion Laboratory Co., Ltd., Japan

[21] Appl. No.: 354,626

[22] Filed: Mar. 4, 1982

[30] Foreign Application Priority Data

Mar. 27, 1981 [JP] Japan .................................. 56-44882

[51] Int. Cl.³ ............................................... A61N 1/34
[52] U.S. Cl. .................................................. 128/1 C
[58] Field of Search ........................ 128/1 C, 421, 422

[56] References Cited

U.S. PATENT DOCUMENTS 2,779,336  1/1957  Abbe ..................................... 128/422
3,762,396  10/1973  Ballentine et al. .................. 128/1 C
3,967,616  7/1976  Ross ..................................... 128/1 C

FOREIGN PATENT DOCUMENTS 2748765  5/1979  Fed. Rep. of Germany ...... 128/1 C
2340743  9/1977  France ................................ 128/1 C

OTHER PUBLICATIONS

"Electrosleep Therapy in the Neurogenic and Psychogenic Disorders" P.C. Clark et al.

Primary Examiner—William E. Kamm
Assistant Examiner—Mitchell J. Shein
Attorney, Agent, or Firm—McGlew and Tuttle

[57] ABSTRACT

An electric sleep inducer comprises a control circuit arranged to produce a therapeutic wave-form output which is applied at frequencies controlled non-stepwise to gradually decrease from 14 Hz to 0 Hz and adapted to a sleep indicating electroencephalogram. The circuit includes cathode and anode conductor elements for applying the therapeutic wave-form output of the control circuit to the head of a subject.

5 Claims, 3 Drawing Figures

ELECTRIC SLEEP INDUCER

BACKGROUND OF THE INVENTION

1. Field of the Invention

This invention relates to an electric sleep inducer and more particularly to an electric sleep inducer arranged to apply an electric current to the head at low frequency values controlled to gradually decrease.

2. Description of the Prior Art

A. History of Electric Sleeping Devices:

It was Gilyarovskii, et al. of the U.S.S.R. who developed an electric sleeping device for the first time. This development stemmed from two ideas. The first one was a novel basic concept of Pavlov concerning sleep. Pavlov was successful in objectively grasping the process of stimulation and inhibition that broadly takes place in the cerebral cortex through his studies of conditional reflex. From this point of view, he was against a then prevalent theory that sleep was brought about by the stimulation of a sleep center and he established a new theory that a sleep represents essentially broadly inhibited state of the cerebral cortex.

The second indea involved electric convulsive therapy and electro-anesthetic therapy which began to be practiced during 1940 or thereabout, in the U.S.A. and England. These electrical therapies were applied to the treatment of mental disorder and were carried out in the following manner: First, a strong electric current of 150 to 250 mA was applied through electrodes positioned on both sides of the head. After that, the current lowered to 60 to 70 mA. Then, the current is either continuously applied at the lowered value or further lowered gradually.

As for a loss of consciousness which was one of the vital phenomena that was caused by the electrical therapy, this can be explained by introducing Pavlov's theory of the inhibited state of the whole cerebral cortex. Therefore, it may be considered that electric sleep therapy in its infancy was derived from the electric convulsive therapy and the electro-anesthetic therapy. It is therefore understandable that Gilyarovskii, et al. stated that the problem to be first solved in establishing electric sleep therapy was how to determine the positions of electrodes for obtaining the strongest effect of a current on the brain.

According to Gilyaroviskii, et al, a fundamental prerequisite to a successful electric sleep therapy is to have a wide inhibition of the cerebral cortex, i.e. to have no disagreeable sensation which prevents sleep from taking place; and on the other hand, it is desirable to apply as large an electric current as possible to a testee so long as the testee complains of no disagreeable feeling.

To satisfy these conditions, Gilyaroviskii, et al stated that, the electric sleeping device must have an electric power of 10 to 12 mA and at least 6 to 8 mA. Accordingly, what is most important is a complaint of the testee about a stimulant sensation. Therefore, while a condition of an electric stimulation suitable for bringing about inhibition over brain cells is considered to be at a frequency value between 1 to 20 Hz, an actual setting of frequency is 100 Hz in many cases.

B. Conventional Electric Sleeping Devices:

The electric sleeping device in its infant stage was arranged to have electrodes thereof applied to the eyes. In view of the structure of the skull, the orbits and the base of the skull, i.e. the eyes and the occiput, were considered most suitable for introducing an electric current into the cerebrum. Further, since a direct current mostly passes on the surface of the endocranium because of resistance of the endocranium, an impulse current has been used because it passes through the endocranium.

However, although positioning the electrodes at the orbit and the occiput certainly most suitably enables the introduction of current into the cerebrum, this arrangement tends to induce a photopsia, because it tends to affect the optic nerve which is very sensitive.

In short, the conventional electric sleep device has been developed by accepting in its entirety the concept of Pavlov that a satisfactory effect can be obtained from an efficient inhibition over the whole area of the cerebral cortex. At the initial stage of the therapy, an impulse of a relatively high frequency of 12 to 16 Hz is applied and then the frequency is gradually lowered to 1-2 Hz according as the working time elapses.

The above stated frequency is lowered in a stepwise manner as shown in FIG. 1 of the accompanying drawings. The stepwise decrease is carried out by manually turning a frequency change-over adjustment dial. The tester verbally inquires of the testee about the electric current stimulation at every step of frequency change-over. This takes much time and labor. Also, in accordance with this stepwise frequency lowering method, the instant at which the frequency is changed presents a problem, because: a difference that thus arises in the stimulation affects the living body to a considerable extent although it is merely a momentary effect. In this regard, a problem into arises since, one of the electrodes is placed on the eye. It has been reported, that there are some moments at which a light is felt with the optic nerve stimulated by the above stated effect which strongly appears at the time of opening and closing of the circuit.

C. The shortcomings of the Conventional Electric Sleep Device:

(1) The conventional electric sleep device requires much time and labor to operate. In determining an optimum galvanic stimulation, the tester depends on complaints from the testee.

(2) The device give excessive stimulation. The stepwise frequency lowering method causes the lowering degree of stimulation to strongly affect a living body, though the change of stimulation is over in a moment.

(3) The device is apt to stimulate the optic nerve. Since one of the electrodes is placed on the eye, the optic nerve which is sensitive is apt to be stimulated in an awakening manner.

(4) The shape of electrodes is complex and thus requires much time in attaching and removing them. One of the electrodes is arranged in a spectacle shape for the orbit while the other is arranged for the occiput. To inhibit the whole area of the cerebral cortex and also for close contact with the head skin, the electrode is provided with many small protrusions. The electrode of this type causes the water content with which it is imbued to quickly dry up. This requires extra care. Besides, the occiput must thoroughly be degreased with alcohol or the like before the electrode is attached to the occiput.

(5) Side effects frequently take place. Since it is a basic concept that a better effect can be obtained by applying the largest allowable electric current within the range of current values that do not cause the testee to complain of a disagreeable feeling under the electrical stimulation given to his head, a strong stimulation tends to be eventually given to the head. Then, this results in a case of photopsia, a skin scald, dizziness and a complication thereof.

(6) The range of adaptive syndrome is apt to be excessively broadened. In other words, as a result of a broadened interpretation of Pavlov's concept, internal diseases, surgical diseases, diseases of the central and peripheral nerve systems, skin diseases, etc. are included in the range of adaptive syndrome. Then, such an excess brings an insomnia treatment out of focus.

The present invention is directed to the obviation of such shortcomings of conventional devices with a novel electric head treating device developed according to a concept which differs from the conventional electric sleep device and is based on findings obtained from the literature on head galvanization and the results of recent great advances in the research of sleep.

SUMMARY OF THE INVENTION

It is therefore a first object of the invention to develop a novel galvanic pulse arrangement which gives a high sleep inducing effect without any side effect and is capable of eliminating the above stated shortcomings of conventional sleep devices.

It is a second object of the invention to determine electric current applying positions and to develop conductor elements suited for the current applying positions.

The development according to the invention is based on the fact that the skin temperature of the hand rises during the process of sleep. The invention has resulted from studies for the mechanism of this fact and the assumption that a decrease in the activity of the sympathetic nervous system serves as a nervous sleep inducing factor. The name of the conventional device "electric sleep device" tends to suggest combined functions of inducing a subject into a sleep state and maintaining the sleep thus induced. However, from the results of recent studies about sleep, it is now generally believed that a humoral factor participates in the duration of the sleeping state. In view of this, the name "electric sleep device" might be considered exaggerative. To avoid this, the device of the present invention is named "an electric sleep inducer". These objects, features and advantages of the invention will become apparent from the following detailed description of an embodiment thereof taken in connection with the accompanying drawings.

DETAILED DESCRIPTION OF PREFERRED EMBODIMENT

Figure 1:
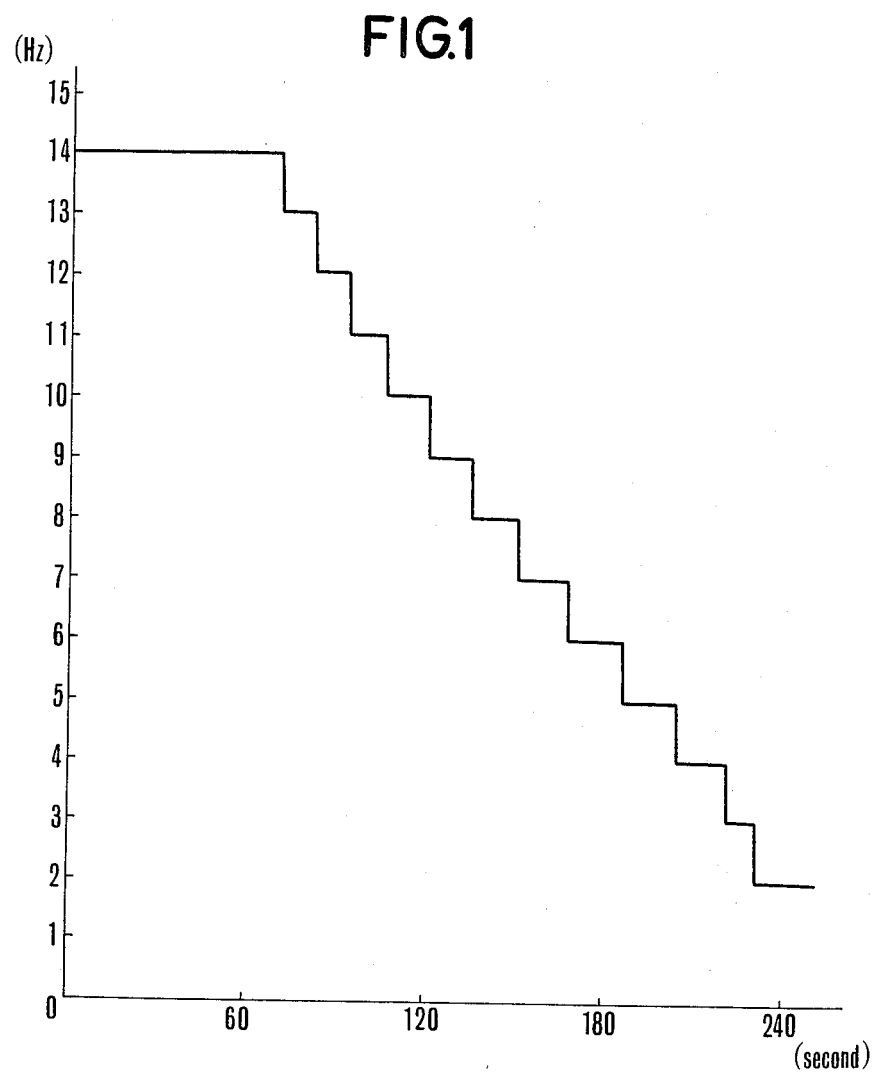
FIG. 1 is an illustration of the pattern of frequencies applied by the conventional electric sleep device.
Figure 2:
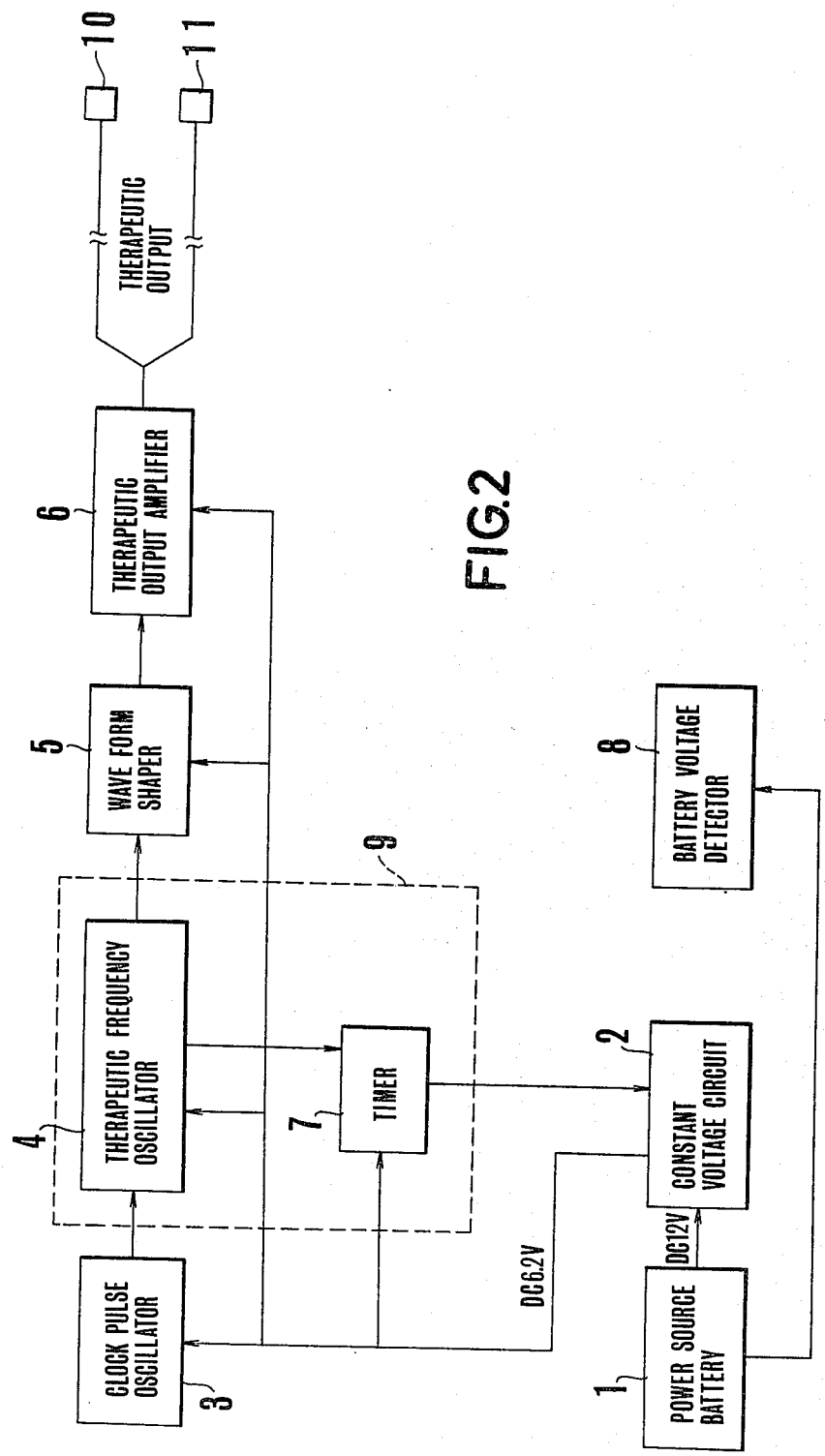
FIG. 2 is a circuit block diagram showing the electric sleep inducer according to the present invention.

In the embodiment shown in FIG. 2, the output of a power source battery 1 is supplied to a pulse oscillator 3, a therapeutic frequency oscillator 4, a wave-form shaper 5, a therapeutic output amplifier 6 and a timer 7 respectively, through a constant voltage circuit 2 which makes the output into a constant voltage. With the output of the power source supplied, each mechanism is actuated. There are provided a voltage detector 8 for the power source battery 1; a micro computer 9 which includes the therapeutic frequency oscillator 4 and the timer 7; and pad like anode and cathode conductor elements 10 and 11 which are connected to the therapeutic output amplifier 6.

Figure 3:
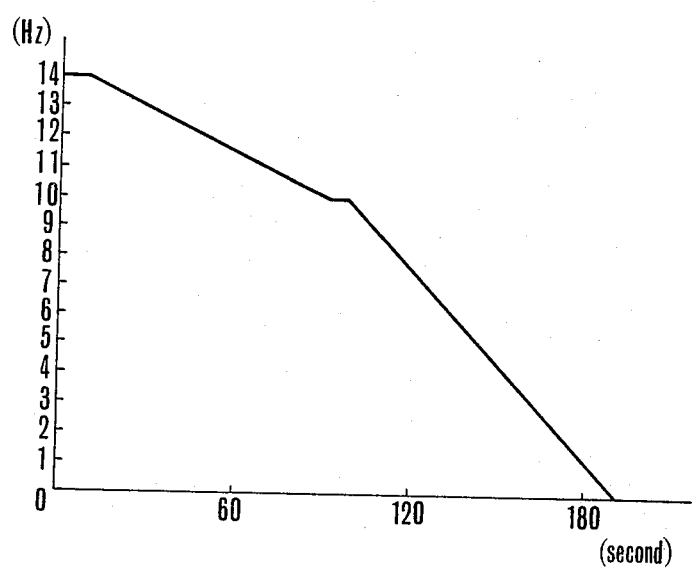
FIG. 3 is an illustration of a therapeutic wave-form pattern obtained in accordance with the present invention.

The embodiment which is arranged as described above operates in the following manner: First, the anode conductor element 10 is wetted with a physiological salt solution and then is applied to the occiput of a testee. Meanwhile, the cathode conductor element 11 is applied to the sinciput. To have the two conductor elements closely in contact with the skin, they are fixed in position with something like a band, etc. After that, the power source is turned on. Therapeutic pulses which are of pulse width 0.2 msec, at 3 to 4 V, and are further controlled by the micro computer 9 to have frequency values of 14 Hz to 0 Hz in a non-stepwise gradually decreasing manner as shown in FIG. 3 is produced from the therapeutic output amplifier 6. The output thus obtained is applied to the head through the conductor elements 10 and 11. As shown in FIG. 3, the therapeutic pulses have 14 to 0 Hz arranged in one cycle in a non-stepwise gradually decreasing manner. The repeating number of this cycle is adjusted according to different degrees of insomnia suffered by the subjects or testees, for example, in the following manner: The micro computer 9 is preset to have an end signal produced to end the treatment by applying the pulses in one cycle or after repeating the cycle several or more times.

The setting of the therapeutic pulses in the non-stepwise gradual decreasing manner is as shown in FIG. 3. First, the frequency of 14 Hz is applied for 10 sec. This period of 10 sec is set because it is an effective length of time for not preventing a slow wave from taking place. Following this, the frequency value is gradually decreased non-stepwise to 10 to 9 Hz spending 80 to 100 sec. In cases where the upper and lower limits of $\alpha$ waves for the subject are 13 Hz and 8 Hz, the values from 10 Hz to 9 Hz are preferable frequency values. Then, the frequency value of 10 Hz to 9 Hz is applied for a period of 7 sec. After that, the frequency value is further lowered to 0 Hz spending a period of time between 90 sec to 100 sec. Thus, in a whole cycle of about 3 min, the pulses which gradually lowers from 14 Hz to 0 Hz are applied to a human body. This arrangement permits the inducement of sleep at a relatively high speed without preventing the occurrence of the $\alpha$ wave which is the lowest frequency of brain activity for awakening.

The advantage of the invention is as follows: With a repeating number of cycles between one to 20 cycles of above stated pattern of non-stepwise gradually decreasing type selectively determined according to an individual difference of human bodies, the pulses are applied for the selected number of cycles to the head of a testee. This effectively induces sleep, with the shortcomings of the conventional method eliminated.

The features and effects of the electric sleep inducer of the present invention are as shown below:

(1) The initial frequency is 14 Hz. This corresponds to the frequency of a spindle wave which appears at the second stage of an NREM (Non Rapid Eye Movement) sleep.

(2) It has been proven that the arrangement to gradually lower the frequency of the applying pulses from 14 Hz to 0 Hz in a non-stepwise manner most effectively introduces a sleep by inhibiting the sympathetic nervous system of a human body.

(3) Although pulses of square wave are used, the width of the pulses applied was set between 0.2 msec and 0.5 msec, because: this pulse width is within the range of chronaxy of the cortex of the head when a stimulation is given at a low voltage between 3 and 4 V and at a low temperature not exceeding 14 Hz. Besides, this pulse width is believed to be within a range for avoiding the occurrence of a photopsia which hinders sleep.

(4) The output voltage is set between 3 and 4 V which is below a threshold value of a stimulus to be felt by the parts of skin at which the current applying electrodes are positioned. This not only minimizes the galvanic sensation but also obviates the possibility of having a local scald on the skin.

(5) The timer incorporated in the micro computer permits repeated pulse applying operations over a period of 30 min or 60 min. It is particularly effective for acceleration of the appearace of a sleeping or sleep indicating electroencephalogram (or a spindle wave) to repeat the above stated non-stepwise gradually decreasing stimulation pattern every three minutes. In other words, with an individual difference taken into consideration, the sleep inducer according to the invention can be set for an operation either over a period of 30 min or 60 min. The sleep inducer then automatically comes to a stop after the lapse of the set time, so that stimulation will never be given over an excessively long period of time.

What is claimed is:

1. An electric sleep inducer comprising:
   a control circuit means for producing a therapeutic wave-form output which is applied at frequency values controlled non-stepwise to gradually decrease from 14 Hz to 0 Hz in a non-stepwise manner and adapted to a sleeping electroencephalogram; and
   cathode and anode conductor means for applying the therapeutic wave-form output of the control circuit to the head.

2. Means for electrically inducing sleep comprising:
   control circuit means for generating a therapeutic wave form having a frequency which gradually decreases from 14 Hz to 0 Hz, said wave form having pulses of 0.2 to 0.5 msec. and from 2 to 4 volts amplitude, said wave form decreasing from 14 Hz to 0 Hz in about 3 minutes; and
   conductor means connected to said circuit means for receiving the wave form including an anode and a cathode both adapted to be connected to a subject's head.

3. Means according to claim 2, wherein said circuit means includes a constant voltage source, an oscillator connected to the constant voltage source, a microcomputer connected to the oscillator and a wave form shaper connected between the microcomputer and said conductor means.

4. A method of electrically inducing sleep comprising applying a wave form to the subject's head through an anode attaced to the occiput of the subject's head and a cathode connected to the sinciput of the subject's head, the wave form being initially at a frequency of about 14 Hz and decreasing smoothly to a frequency of 0 Hz over a period of about 3 minutes, the wave form having pulses of duration between 0.2 and 0.5 msec, and between 3 and 4 volts.

5. A method according to claim 4, wherein the frequency of 14 Hz is maintained for about 10 seconds, the frequency is reduced to between 10 and 9 Hz over a period of about 80 to 90 seconds and maintained for a duration of about 7 seconds, and the frequency is reduced from the range of 10 to 9 Hz to 0 over a period of about 90 to 100 seconds.

* * * * *